United States Patent [19]

Flury et al.

[11] Patent Number: 5,130,452
[45] Date of Patent: Jul. 14, 1992

[54] PHOSPHORUS COMPONDS AND THEIR USE AS FLAME RETARDANT FOR POLYMERS

[75] Inventors: Peter Flury, Himmelried, Switzerland; Wolfgang Scharf, Grenzach-Wyhlen, Fed. Rep. of Germany

[73] Assignee: Ciba-Geigy Corporation, Ardsley, N.Y.

[21] Appl. No.: 695,856

[22] Filed: May 6, 1991

[30] Foreign Application Priority Data

May 9, 1990 [CH] Switzerland .................. 1570/90

[51] Int. Cl.⁵ .................. C07F 9/06; C08K 5/52
[52] U.S. Cl. .................. 558/211; 524/127; 524/140; 524/151; 558/83
[58] Field of Search .................. 558/83, 211

[56] References Cited

U.S. PATENT DOCUMENTS

| | | | |
|---|---|---|---|
| 3,689,602 | 9/1972 | Ismail | 558/85 |
| 4,370,281 | 1/1983 | Clubley et al. | 558/211 |
| 4,749,645 | 6/1988 | Goddard et al. | 430/551 |

FOREIGN PATENT DOCUMENTS

| | | |
|---|---|---|
| 2371455 | 6/1978 | France . |
| 1024641 | 3/1966 | United Kingdom . |
| 1512165 | 5/1978 | United Kingdom . |
| 2089350 | 6/1982 | United Kingdom . |

*Primary Examiner*—Paul R. Michl
*Assistant Examiner*—Tae H. Yoon
*Attorney, Agent, or Firm*—Luther A. R. Hall

[57] ABSTRACT

Compounds of general formula I

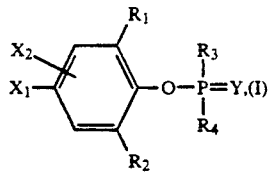

wherein
 $X_1$ is chloro or bromo,
 $X_2$ is chloro, bromo or hydrogen, and
 Y is O or S, and
 $R_1$ and $R_2$ are each independently of the other $C_1$-$C_4$alkyl, and
 $R_3$ and $R_4$ is a group of formula II

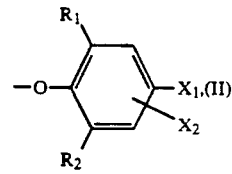

which carries identical or different substituents and wherein $R_1$, $R_2$, $X_1$ and $X_2$ are as defined above, or $R_3$ and $R_4$, when taken together, form a group of formula III

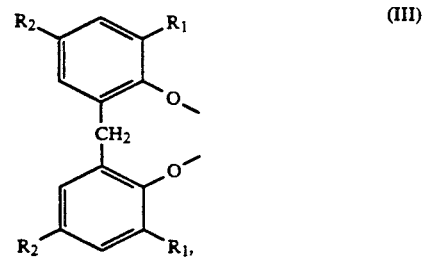

wherein $R_1$ and $R_2$ are as defined above, are very suitable flame retardants for polymers.

14 Claims, No Drawings

PHOSPHORUS COMPONDS AND THEIR USE AS FLAME RETARDANT FOR POLYMERS

The present invention relates to novel phosphorus compounds, to polymers containing them, and to the use of said novel phosphorus compounds as flame retardants for polymers.

Polymers are commonly made more flame-resistant by reducing the organic component, for example by adding fillers which are non-flammable or of low flammability, for example quartz flour, glass, wollastonite and the like. However, the amount of filler added must be substantial in order to ensure adequate flame-resistance, with the consequence that insoluble problems often arise during the preparation and processing of the reaction resin compositions.

Another possibility is the addition of flame retardants to the polymers. Suitable flame retardants are inorganic compounds such as boron compounds or metal hydroxides. In this case too it is necessary to add large amounts of such modifiers, again with adverse consequences for the preparation and processing of the polymers. The use of perhalogenated compounds such as tetrabromobisphenol A, decabromodiphenyl ether or perbrominated polystyrenes is highly contentious, as the disposal of such polymers is environmentally hazardous. There is the potential danger of the formation of highly toxic (dioxin-type) products during incineration.

Halogenated phosphoric acid esters are disclosed as flame retardant additives for plastics materials in U.S. Pat. No. 3,689,602.

The use of flame retardant organophosphorus compound which are not incorporated in the polymers results in a kind of plasticising effect, which often leads to a substantial loss of mechanical and electrical properties of the polymers so treated. For example, the mechanical strength and glass transition temperature are reduced by the plasticising action of the organophosphorus compound. In addition, these compounds are unstable to hydrolysis, resulting in an increased water absorption of the reaction resin moulding material and simultaneous formation of different phosphorus compounds. Halogen-free sterically hindered phosphonates and phosphates are disclosed as image dye stabilisers for photographic layers in EP-A-265 196.

Surprisingly, it has now been found that novel sterically hindered phosphates and thiophosphates having a low halogen content enhance the flame resistance of polymers without substantially effecting their other properties such as heat resistance, mechanical strength, dielectric constant or water absorption. The novel flame retardants have excellent stability to heat and hydrolysis.

The present invention relates to compounds of general formula I

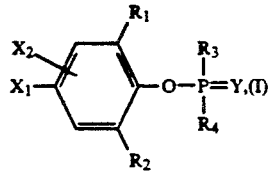

wherein
$X_1$ is chloro or bromo,
$X_2$ is chloro, bromo or hydrogen, and
Y is O or S, and
$R_1$ and $R_2$ are each independently of the other $C_1$-$C_4$alkyl, and
$R_3$ and $R_4$ is a group of formula II

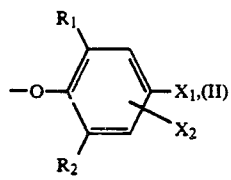

which carries identical or different substituents and wherein $R_1$, $R_2$, $X_1$ and $X_2$ are as defined above, or $R_3$ and $R_4$, when taken together, form a group of formula III

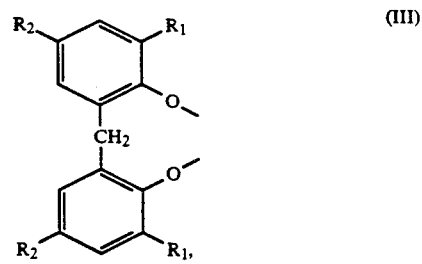

wherein $R_1$ and $R_2$ are as defined above.

$X_1$ and $X_2$ are chloro and, preferably, bromo. The particularly preferred meaning of $X_2$ is hydrogen.

Y may be O or S. Preferably Y is O.

$R_1$ and $R_2$ as alkyl substituents may be each independently of the other typically methyl, ethyl, isopropyl or tert-butyl. $R_1$ in formulae I and II is preferably methyl or tert-butyl. The preferred meaning of $R_2$ is methyl.

In preferred compounds of formula I the substituents $R_3$ and $R_4$ are a group of formula II. In particularly preferred compounds these groups are identical. These compounds are so-called symmetrical phosphates.

On account of their low halogen content, those compounds are also of especial interest in which $R_3$ and $R_4$ together form a group of formula III. In this formula, $R_1$ is preferably tert-butyl and $R_2$ is preferably methyl.

The compounds of formula I are prepared in a manner which is known per se.

Compounds of formula I, wherein Y is O and $R_3$ and $R_4$ are a group of formula II, may be prepared by reacting at least one phenol of formula IV

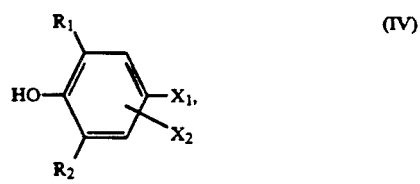

wherein $R_1$, $R_2$, $X_1$ and $X_2$ are as defined above, with $PCl_3$ in the overall ratio of ca. 3:1, in the presence of a base such as triethylamine or pyridine, and in an inert solvent such as toluene. If it is desired to prepare the corresponding phosphates in which Y=O, the resultant phosphite of formula V

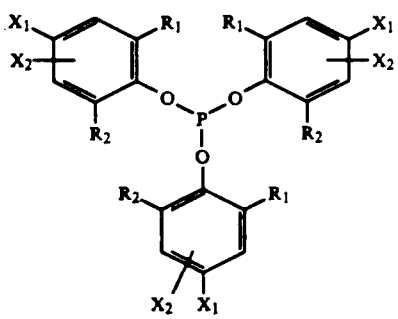

is oxidised by conventional methods, for example with peracetic acid and hydrogen peroxide, to the phosphate of formula I.

The corresponding thiophosphate in which Y=S is obtained is known manner by reacting the phosphite of formula V with elemental sulfur (q.v. for example Houben-Weyl "Methoden der organischen Chemie", Vol. 12/2, p. 647).

The compounds of formula I, wherein Y is O and $R_3$ and $R_4$ together form a group of formula III, can also be prepared in known manner (q.v. for example EP-A 265 196), by reacting a bisphenol of formula VI

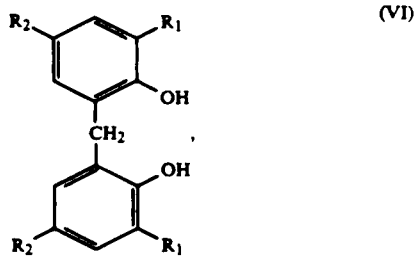

wherein $R_1$ and $R_2$ are as defined above, with a phosphoric acid dichloride of formula VII

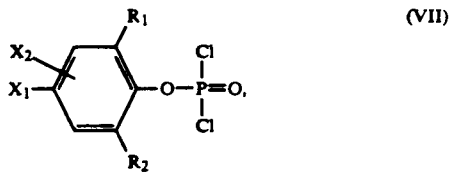

in the presence of a base and in an inert solvent, at elevated temperature.

The phosphoric acid dichloride of formula VII can be prepared by reacting a phenol of formula IV with $POCl_3$.

The phenols of formula IV are prepared in known manner from the appropriate non-halogenated phenols with elemental halogen, for example by the dropwise addition of elemental bromine to a solution of the phenol in an inert solvent such as toluene.

If it is desired to prepare compounds of formula I, wherein X is S and $R_3$ and $R_4$ together form a group of formula III, then it is preferred to react a bisphenol of formula VI with $PCl_3$. The phosphorus acid dichloride so obtained is subsequently reacted with a phenol of formula IV to the corresponding phosphite which, as described above, is reacted with elemental sulfur to the corresponding thiophosphate of formula I.

The compounds of formula I are suitable flame retardants for polymers, especially for epoxy resins.

The amount of compound of formula I added to the polymer as a flame retardant may be varied over a wide range. Usually from 0.1 to 100 parts by weight are used per 100 parts by weight of polymer. Preferably 0.5 to 30 parts are used and, most preferably, from 2 to 20 parts by weight of compound of formula I per 100 parts by weight of polymer. The optimum amount used depends on the nature of the polymer and the nature of the compound of formula I and may be readily determined by simple experimentation. However, because the compounds of formula I are generally effective at low levels of addition and are furthermore are of low halogen content, they produce less unwanted effects in the polymer than other known flame retardant additives.

The compounds of formula I may be used in various physical forms depending on the polymer used and the desired properties. For instance they may be ground to a finely divided form to enable better dispersion throughout the polymer. If desired, mixtures of different compounds of formula I may also be used.

The compounds of formula I may be used in various polymers. Examples of polymers which may be rendered flame retardent are:

1. Polyphenylene oxides and sulfides, and blends of these polymers with polystyrene graft polymers or styrene copolymers such as high impact polystyrene, EPDM copolymers with rubbers, as well as blends of polyphenylene oxide with polyamides and polyesters.

2. Polyurethanes which are derived from polyethers, polyesters or polybutadiene with terminal hydroxyl groups on the one hand and aliphatic or aromatic polyisocyanates on the other hand including polyisocyanurates, as well as precursors thereof.

3. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalamide or poly-m-phenylene iso-phthalamide, as well as copolymers thereof with polyethers, such as with polyethylene glycol, polypropylene glycol or polytetramethylene glycols.

4. Polyesters which are derived from dicarboxylic acids and di-alcohols and/or from hydroxycarboxylic acids or the corresponding lactones, such as polyethylene terephthalate, polybutylene terephthalate, poly-1,4-dimethylol-cyclohexane terephthalate and polyhydroxybenzoates as well as block-copolyether-esters derived from polyethers having hydroxyl end groups.

5. Unsaturated polyester resins which are derived from copolyesters of saturated and unsaturated dicarboxylic acids with polyhydric alcohols and vinyl compounds as cross-linking agents.

6. Polystyrene.

7. Graft copolymers of styrene, for example styrene on polybutadiene, styrene and acrylonitrile on polybutadiene, styrene ad alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with random copolymers of styrene or α-methylstyrene with dienes or acrylic derivatives, for instance the terpolymers of styrene known as ABS, MBS, ASA or AES terpolymers.

8. Cross-linked epoxy resins which are derived from polyepoxides, for example, from bis-glycidyl ethers, especially bisphenol A diglycidyl ethers, or from cycloalphatic diepoxides.

9. Polycarbonates.

The crosslinked epoxy resins are particularly suitable.

Hence the present invention also relates to compositions containing a polymer and at least one compound of formula I.

The compositions of the invention may also contain other conventional modifiers such as heat stabilisers, ultraviolet light absorbers, antioxidants, antistatic agents, preservatives, adhesion promoters, fillers, pigments, lubricants, blowing agents, fungicides, plasticisers, processing aids, other fire-retardant additives and smoke suppressants.

Other fire retardant additives which may be used with the compounds of formula I include phosphorus containing salts such as ammonium polyphosphate, antimony oxide, hydrated alumina, bismuth oxide, molybdenum oxide, or mixtures of these compounds with zinc and/or magnesium oxide or salts.

The invention is illustrated in more detail by the following Examples.

EXAMPLE 1

244.4 g (2.0 mol) of 2,6-dimethylphenol are charged to 600 ml of toluene. With stirring, 329.2 g (2.06 mol) of bromine are added dropwise to this solution at 20° C. over 45 minutes. After stirring for a further 5 minutes at room temperature, 5 ml of pyridine are added, followed by the addition over 10 minutes of 91.6 g (0.666 mol) of phosphorus trichloride. The reaction mixture is slowly heated over half an hour to reflux temperature and then kept at this temperature of 2.5 hours, with evolution of HCl and HBr (neutralisation in a wash unit).

Still at reflux temperature, 70 ml of triethylamine are added dropwise over 5 minutes and the reaction mixture is cooled after 15 minutes to 15° C.

Oxidation is carried out at room temperature by addition of 200 ml of acetic acid over 15 minutes, followed by the dropwise addition of 90.4 ml of hydrogen peroxide (30%) at 15°-20° C. over 1 hour and 45 minutes. The reaction mixture is efficiently stirred for 2 hours at room temperature, 600 ml of water are added, and the toluene is stripped off by steam distillation. After filtration at room temperature, the product is washed with water and then with methanol. The colourless crystals so obtained are vacuum dried at 80° C. and have a melting point of 170° C. Yield: 424 g (98% of theory).

The resultant product is tris(4-bromo-2,6-dimethylphenyl)phosphate.

EXAMPLE 2

With stirring, 32.0 g (0.2 mol) of bromine are added to 24.43 g (0.2 mol) of 2,6-dimethylphenol in 200 ml of toluene over 45 minutes. After stirring for a further 10 minutes, 68.1 g (0.2 mol) of 2,2'-methylenebis(4-methyl-6-tert-butylphenol) and 2 ml of pyridine are added. Then 27.5 g (0.2 mol) of phosphorus trichloride are added dropwise. The reaction mixture is then slowly heated to reflux temperature over 1 hour, kept at this temperature for 2 hours with stirring, and then 25 ml of triethylamine are slowly added dropwise. After 20 minutes the reaction mixture is cooled to 15° C. Oxidation is carried out as in Example 1 with 70 ml of acetic acid and 30.2 ml (0.27 mol) of hydrogen peroxide (30%, giving 110 g (94% of theory) of a colourless powder with a melting point of 240° C.

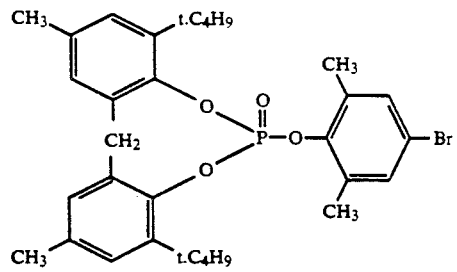

EXAMPLE 3

The general procedure described in Example 1 is repeated to give 48 g (93% of theory) of a colourless powder with a melting point of 173° C. 2,6-Dimethylphenol is replaced by 2-tert-butyl-6-methylphenol. The resultant produce is tris(4-bromo-2-tert-butyl-6-methylphenyl)phosphate.

EXAMPLE 4

Test specimens (2 mm sheets) are prepared from the following epoxy resin to which flame retardants of Examples of 1 to 3 added:

100 parts by weight of bisphenol A diglycidyl ether (epoxy value 5.6 eq/kg)

10 parts by weight of a mixture of 25 parts by weight of dicyandiamide and 75 parts by weight of oligomeric cyanoguanidine (from EP-A 306 451, Ex. 3)

0.3 parts by weight of 2-methylimidazole 15 parts by weight of flame retardant.

The specimens are cured for 1 hour at 160° C. and for 2 hours at 180° C. to give a yellowish clear epoxy resin.

After removal from the mould, the specimens are tested for their flammability in accordance with the standard of Underwriters Laboratories Inc. UCL 94, third edition (revised) of Sep. 25, 1981 (horizontal burn test).

In addition, the glass transition temperature is determined by the DSC method (differential scanning calorimetry). The boiling water absorption is also determined.

A thermogravimetric analysis is also carried out, in which the temperature is determined at which the specimen exhibits a weight loss of 5 and 10% respectively.

The results are summarised in Table 1.

TABLE 1

| Flame retardant according to Example | — | 1 | 2 | 3 |
|---|---|---|---|---|
| flame inhibition according to UL at 2 mm | burns | V-O | V-O | V-O |
| glass transition temperature (DSC) [°C.] | 150 | 142 | 144 | 140 |
| boiling water absorption (2 mm/1 h) [% by weight] | 0.39 | 0.33 | 0.30 | 0.29 |
| thermogravimetric analysis | | | | |
| t (−5% by weight) [°C.] | 325 | 300 | 290 | 305 |
| t (−10% by weight) [°C.] | 345 | 315 | 305 | 320 |

What is claimed is:

1. A compound of formula I

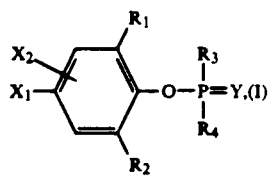

wherein $X_1$ is chloro or bromo, $X_2$ is chloro, bromo or hydrogen, and

Y is O or S, and $R_1$ and $R_2$ are each independently of the other $C_1$-$C_4$alkyl, and $R_3$ and $R_4$ is a group of formula II

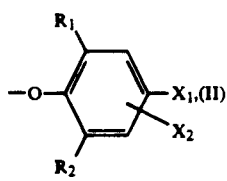

which carries identical or different substituents and wherein $R_1$, $R_2$, $X_1$ and $X_2$ are as defined above, or $R_3$ and $R_4$, when taken together, form a group of formula III

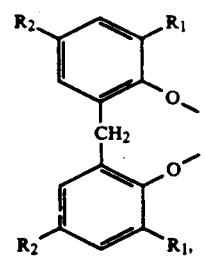

wherein $R_1$ and $R_2$ are as defined above.

2. A compound according to claim 1, wherein $X_1$ is bromo.

3. A compound according to claim 1, wherein $X_2$ is hydrogen.

4. A compound according to claim 1, wherein Y is oxygen.

5. A compound according to claim 1, wherein $R_1$ and $R_2$ are each independently of the other methyl, ethyl, isopropyl or tert-butyl.

6. A compound according to claim 1, wherein $R_1$ in formulae I and II is methyl or tert-butyl.

7. A compound according to claim 1, wherein $R_1$ in formula III is tert-butyl.

8. A compound according to claim 1, wherein $R_2$ is methyl.

9. A compound according to claim 1, wherein $R_3$ and $R_4$ are each a group of formula II which carries identical or different substituents.

10. A compound according to claim 1, wherein $R_3$ and $R_4$ together form a group of formula III.

11. A composition comprising a polymer and at least one compound of formula I according to claim 1.

12. A composition according to claim 15 comprising 0.1 to 100 parts by weight of a compound of formula I, based on 100 parts by weight of polymer.

13. A composition according to claim 15 comprising an epoxy resin.

14. A method of rendering polymers flame retardant by using a compound of formula I according to claim 1 as flame retardant.

* * * * *